Figure 1:
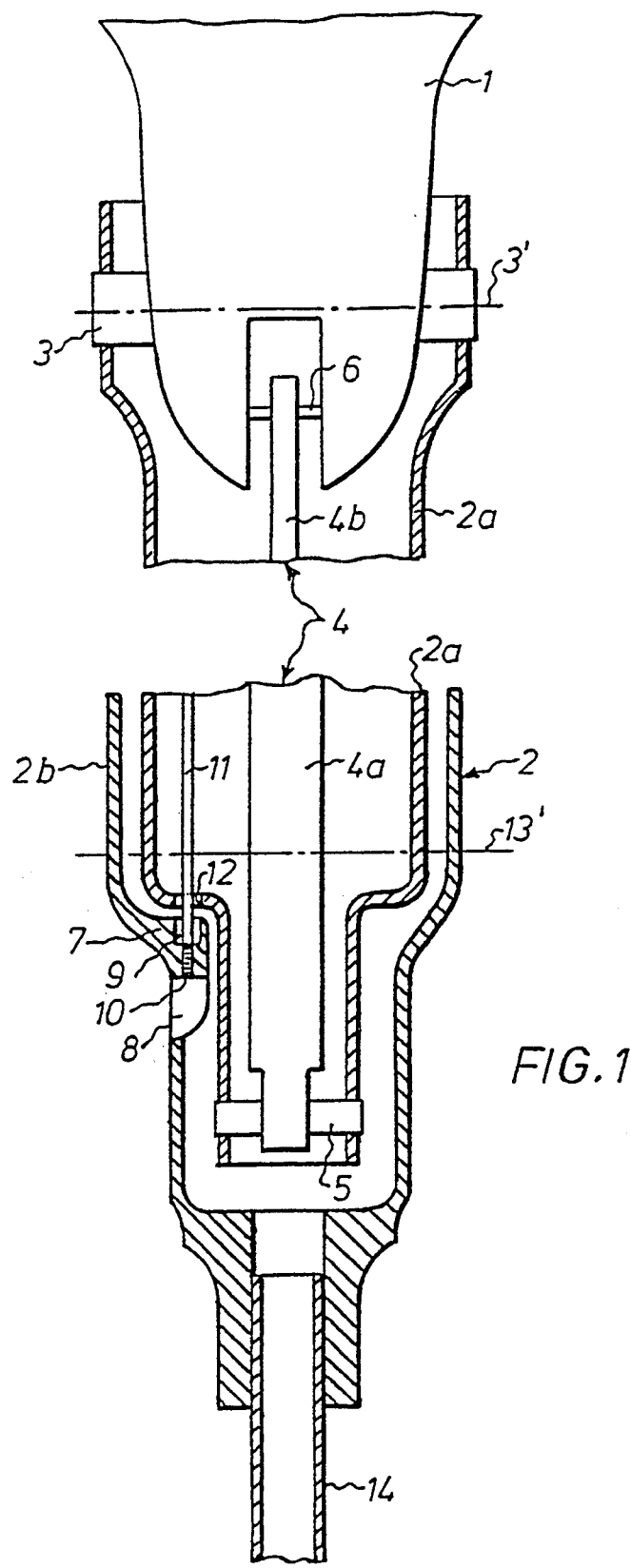

United States Patent [19]

Stenberg

[11] Patent Number: 5,376,136
[45] Date of Patent: Dec. 27, 1994

[54] ARTIFICIAL LEG WITH TWO PARTS ARTICULATED LOWER LEG

[75] Inventor: Karl-Erik Stenberg, Växjö, Sweden

[73] Assignee: Vaxjo-Protes AB, Vaxjo, Sweden

[21] Appl. No.: 965,257

[22] PCT Filed: Jun. 20, 1991

[86] PCT No.: PCT/SE91/00446
§ 371 Date: Jan. 7, 1993
§ 102(e) Date: Jan. 7, 1993

[87] PCT Pub. No.: WO91/19467
PCT Pub. Date: Dec. 26, 1991

[30] Foreign Application Priority Data

Jun. 21, 1990 [SE] Sweden ................................ 9002220

[51] Int. Cl.$^5$ ................................ A61F 2/64
[52] U.S. Cl. ........................ 623/44; 623/43
[58] Field of Search ..................... 623/39–46, 623/26, 27

[56] References Cited

U.S. PATENT DOCUMENTS

| 2,480,856 | 9/1949 | Henschke et al. | 623/26 |
| 3,309,715 | 3/1967 | Nader et al. | |
| 3,551,915 | 1/1971 | Woodall | |
| 3,806,958 | 4/1974 | Gusev | 623/44 X |

FOREIGN PATENT DOCUMENTS

| 1246301 | 12/1988 | Canada |  |
| 2507501 | 6/1980 | Germany |  |
| 333430 | 3/1971 | Sweden |  |
| 1225566 | 4/1986 | U.S.S.R. | 623/39 |

OTHER PUBLICATIONS

Abstract of Soviet Union Patent SU 1533-686-A Dec. 1989.

Primary Examiner—David H. Willse
Attorney, Agent, or Firm—Luedeka, Neely & Graham

[57] ABSTRACT

An artificial leg has a femoral member (1); a lower-leg member (2) articulated to the femoral member about a knee joint axis (3') and adapted for connection to a prosthetic foot; and a hydraulic device (4) for controlling the knee joint functions of the artificial leg. The hydraulic device comprises a cylinder member (4a) which is articulated to the lower-leg member, and a piston rod (4b) which is articulated to the femoral member. The hydraulic device (4) is operated by an operating rod (11). The lower-leg member consists of an upper part (2a) which is articulated to the femoral member (1) and supports the hydraulic device (4) whose cylinder member (4a) is articulated to the upper part, and a lower part (2b) which is adapted for connection to the prosthetic foot and to which the operating rod (11) is connected. The upper part (2a) is articulated to the lower part (2b) about a pivot pin (13) located in front of the knee joint axis (3') to which it is parallel, to be pivoted relative to the lower member. Thus, the upper part (2a) is pivotable between a rear position in which the operating rod (11) acts upon the hydraulic device (4) for locking the pivotal movement of the upper part (2a) about the knee joint axis (3'), and a frontal position in which the operating rod (11) acts upon the hydraulic device (4) to release the locking.

6 Claims, 2 Drawing Sheets

ARTIFICIAL LEG WITH TWO PARTS ARTICULATED LOWER LEG

The present invention relates to an artificial leg having a femoral member; a lower-leg member articulated to said femoral member about a knee joint axis and adapted for connection to a prosthetic foot; and a locking mechanism adapted to releasably lock the pivotal movement of said lower-leg member about said knee joint axis and operable by means of an operating member.

In a prior art artificial leg of this type, the locking mechanism consists of a hydraulic device comprising a cylinder member which is articulated to the lower-leg member, and a piston rod which is articulated to the femoral member and which is operated by means of an operating rod adapted for connection to the prosthetic foot. Since the operating rod is to be connected to the prosthetic foot, the latter must be of a special design, and the artificial leg can thus only by mounted on a specific type of prosthetic feet available on the market. In addition, it is difficult to adapt the prior art artificial leg to the length of the user. A further disadvantage of the prior art artificial leg is that its locking mechanism (which serves to lock the knee joint, i.e. to prevent the lower-leg member from pivoting relative to the femoral member about the knee joint axis when the prosthetic foot is applied against the ground) does not release the locking until the prosthetic foot is lifted from the ground. Thus, the user must lift the artificial leg in a locked, stretched position when walking, thereby waddling like a duck.

The object of the present invention is to provide an artificial leg which is of the type described above and which is so designed that the above-mentioned disadvantages are obviated, i.e. designed in such a manner that it can easily be mounted on different types of prosthetic feet available on the market as well as be adapted to the length of the user, and that the user will not waddle like a duck.

According to the invention, this object is achieved by an artificial leg which is of the type described above and which is characterised in that the lower-leg member consists of an upper part which is articulated to the femoral member and supports the locking mechanism, and a lower part which is adapted for connection to the prosthetic foot and to which the operating member is connected, and that the upper part is articulated to the lower part about a pivot pin located in front of the knee joint axis to which it is parallel, to be pivoted relative to said lower part between a rear position in which the operating member connected to the lower part acts upon the locking mechanism for locking the pivotal movement of the upper part about the knee joint axis, and a frontal position in which the operating member acts upon the locking mechanism to release said locking.

The upper and the lower part are suitably tubular, the lower portion of the upper part being preferably inserted into the upper portion of the lower part, so that said upper part, when in its rear position, is applied against the rear wall of said lower part and, when in its frontal position, is applied against the front wall of said lower part.

The locking mechanism preferably is a hydraulic device having a cylinder member which is articulated to said upper part, and a piston rod which is articulated to said femoral member, said operating member being an operating rod.

Figure 2:
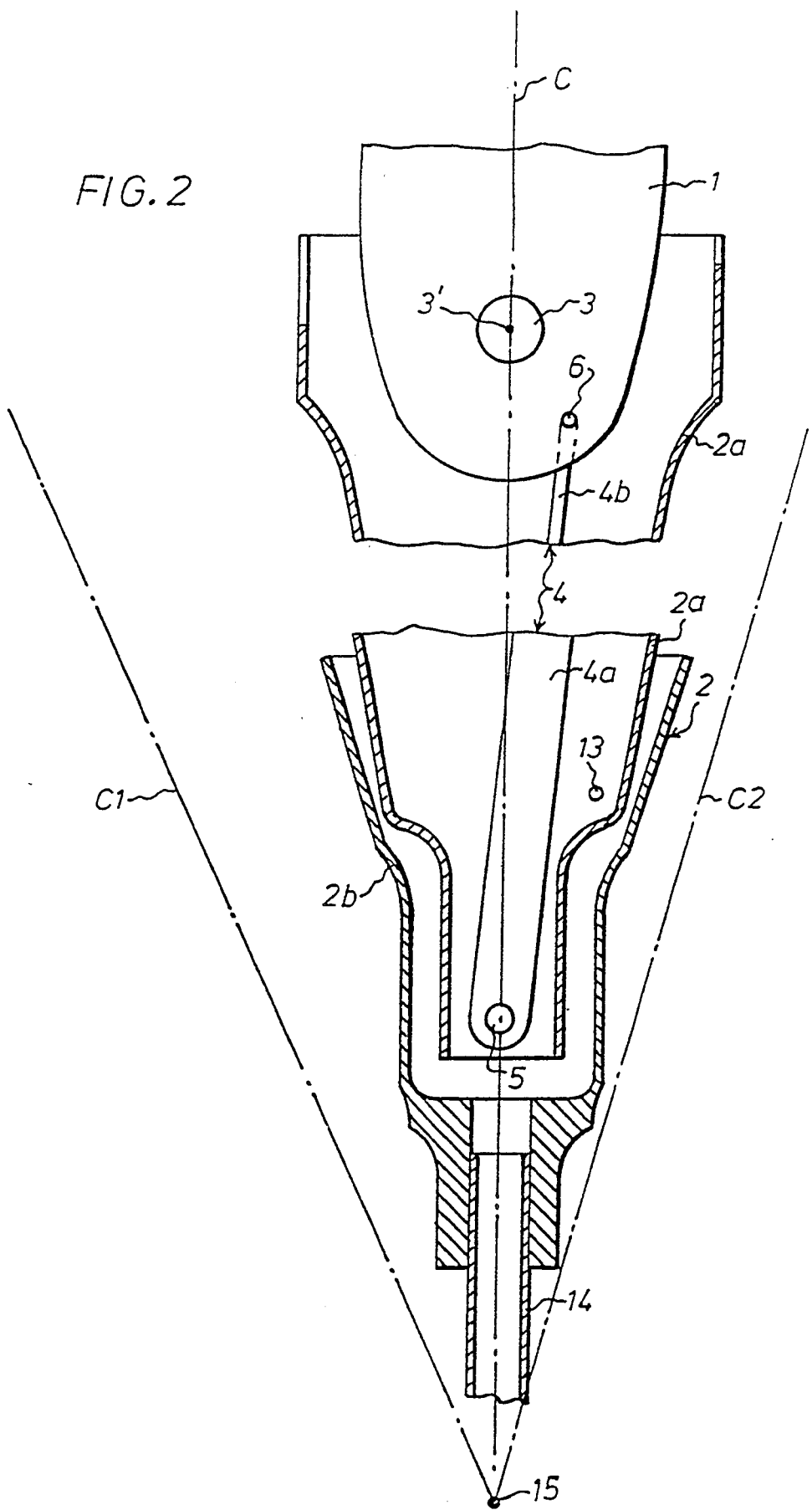

The invention will now be described in more detail below, reference being had to the accompanying drawings, in which FIG. 1 illustrates an artificial leg according to the invention in a longitudinal section parallel to the knee joint axis of the artificial leg, and FIG. 2 illustrates the artificial leg in a longitudinal section perpendicular to the knee joint axis.

The artificial leg illustrated in the drawings has a femoral member 1, of which only the lower portion is shown, and a lower-leg member 2 which consists of a tubular upper part 2a and a tubular lower part 2b. The femoral member 1 extends a short distance down into the upper part 2a, and is articulated thereto by means of a transverse pivot pin 3 defining the knee joint axis 3' of the artificial leg.

The upper part 2a accommodates and supports a hydraulic device 4 for controlling the knee joint functions of the artificial leg. The hydraulic device 4 is advantageously of the type disclosed in SE Patent Specification 8500740-9 which corresponds to U.S. Pat. No. 4,662,486 issues May 5, 1987, the disclosure of which is hereby incorporated in toto. The hydraulic device 4 comprises a cylinder member 4a which, by means of a pivot pin 5 parallel to the pivot pin 3, is articulated to the lower portion of the upper part 2a, as well as a piston rod 4b which, by means of a pivot pin 6 parallel to the pivot pins 3 and 5, is articulated to the lower portion of the femoral member 1. The pivot pins 3 and 5 are situated on a vertical line C, whereas the pivot pin 6 is located slightly in front of this line (see FIG. 2).

The outer cross-sectional dimensions of the lower portion of the upper part 2a are smaller than the inner cross-sectional dimensions of the upper portion of the lower part 2b. The lower portion of the upper part 2a is inserted into the upper portion of the lower part 2b.

The upper portion of the lower part 2b is formed with a shoulder 7 and a recess 8 located below the shoulder. A vertical hole 9, whose lower part is threaded, extends through the shoulder 7. A screw 10 is screwed a short distance into the hole 9 from below. The lower end of an operating rod 11 for controlling the hydraulic device 4 is inserted from above into the hole 9 via a hole 12 in the lower portion of the upper part 2a and is applied against the screw 10 by a spring (not shown) in the hydraulic device 4. The position of the operating rod 11 is accurately set with the aid of the screw 10.

The upper part 2a is articulated to the lower part 2b about a pivot pin 13 situated in front of the knee joint axis 3' to which it is parallel. The pivot pin 13 extends through the side walls of the upper part 2a at the lower portion thereof, and is mounted in the side walls of the lower part 2b at the upper portion thereof. The vertical position of the axis 13' of the pivot pin 13 is indicated by a dash-dot line in FIG. 1. The upper part 2a is pivotable relative to the lower part 2b between a rear position and a frontal position. In FIG. 2, the upper part 2a is in an intermediate position. As is apparent from FIG. 2, the front wall and the rear wall in the upper portion of the lower part 2b slightly diverge upwards in relation to the front and the rear wall in the lower portion of the upper part 2a. In the rear position, the rear wall of the lower portion of the upper part 2a is applied against the rear wall of the upper portion of the lower part 2b. In the frontal position, the front wall of the lower portion of the upper part is applied against the front wall of the upper portion of the lower part. If desired, a plate (not shown) of a cushioning, elastic material may be placed in the space between the front walls of the two parts 2a and 2b, as well as in the space between the rear walls thereof.

When the upper part 2a, to which the hydraulic device 4 is connected, is pivoted about the pivot pin 13 relative to the lower part 2b, to which the operating rod 11 is connected, the operating rod 11 is moved relative to the hydraulic device 4 to operate the latter. By means of the screw 10, the operating rod 11 has been set so as to actuate the hydraulic device 4, when the upper part 2a is in its rear position, so that this device locks the knee joint, i.e. prevents the femoral member 1 and the lower-leg member 2 from pivoting in relation to one another about the pivot pin 3, and so as to actuate the hydraulic device 4, when the upper part is in its frontal position, to permit pivotal movement of the femoral member 1 and the lower-leg member 2 in relation to one another about the pivot pin 3.

The lower part 2b is connected to a prosthetic foot (not shown) by a tube 14. Thus, the tube 14, which at its lower end is connected to the prosthetic foot, is cut to a length suiting the user, and is subsequently fixed to the lower portion of the lower part 2b. The position of the ankle joint axis of the prosthetic foot is illustrated by the reference numeral 15 in FIG. 2.

Since the hydraulic device 4 and its operating rod 11 are incorporated in the lower-leg member 2 in which they form a previously set unit which need not, as in prior art artificial legs, be connected to the prosthetic foot and adjusted thereto, the artificial leg is conveniently mounted on different types of prosthetic feet available on the market by means of the connecting tube 14. The length of the artificial leg can be adapted to the length of the user by choosing a connecting tube 14 of suitable length. Consequently, the lower-leg member 2 need not be adjusted, and may thus be of standard design regardless of the length of the artificial-leg user.

When the user applies the prosthetic foot against the ground when walking, with a straight or stretched artificial leg, as illustrated schematically by a dash-dot line C1 in FIG. 2, the upper part 2a is in its rear position, which means that the knee joint is locked. When, during the walking cycle, the straight and loaded artificial leg then is swung forwards about the ankle joint axis 15, the knee joint remains in locked position for as long as the line of load is situated behind the pivot pin 13 and the upper part 2a thus is in its rear position. As soon as the straight and loaded artificial leg passes the position schematically illustrated by a dash-dot line C2 in FIG. 2, in which the line of load passes the pivot pin 13 to be situated in front of said pin, the upper part 2a is swung to its frontal position, thereby releasing the knee joint so that the artificial leg can be bent. Thus, the artificial leg can be bent before the load has entirely disappeared owing to the prosthetic foot being lifted from the ground, so that the artificial leg need not be lifted in a locked and straight position. In this manner, there will be no waddling gait.

I claim:

1. An artificial leg having a femoral member (1); a lower-leg member (2) articulated to said femoral member about a knee joint axis (3') and adapted for connection to a prosthetic foot; and a locking mechanism (4) adapted to releasably secure said lower-leg member from pivotable movement about said knee joint axis by means of an operating member (11); said lower-leg member (2) comprising an upper part and a lower part, each part having an upper portion and a lower portion, said upper portion of said lower-leg upper part being articulated to said femoral member about a first pivot axis (3) corresponding to said knee joint axis; said locking mechanism (4) being length variable between upper and lower ends thereof and articulated at said lower end to the lower portion of the lower-leg upper part (2a) about a second pivot axis (5) substantially parallel to said first pivot axis (3) and articulated at the upper end thereof to said femoral member (1) about a third pivot axis (6), also substantially parallel to said first pivot axis said third pivot axis (6) being forward of an axis (c) between said first and second pivot axes; said lower-leg lower part (2b) being articulated to said lower-leg upper part about a fourth pivot axis (13) substantially parallel to said first pivot axis positioned proximate of said second pivot axis (5) and forward of said axis (c) between said first and second pivot axes, the lower end of said lower-leg lower part being adapted to receive a prosthetic foot; said operating member (11) being connected between said lower-leg lower part and said locking mechanism for controlling said locking mechanism to selectively lock said lower leg upper part from pivotal movement about said first pivot axis.

2. The artificial leg of claim 1 wherein the lower-leg upper part (2a) is tubular.

3. The artificial leg of claim 2 wherein the lower-leg lower part (2b) is tubular.

4. The artificial leg of claim 3 wherein the lower portion of the lower-leg upper part (2a) is inserted into the upper portion of the lower-leg lower part (2b), so that said lower-leg upper part, when in a walking cycle rear position, is applied against the rear wall of said lower-leg lower part and, when in a walking cycle front position, is applied against the front wall of said lower-leg lower part.

5. The artificial leg of claim 1 wherein the locking mechanism (4) is a hydraulic device having a cylinder member (4a) which is articulated to said lower-leg upper part (2a), and a piston rod (4b) which is articulated to said femoral member (I), said operating member (11) being an operating rod adjustably secured to said lower-leg lower part (2b).

6. The artificial leg of claim 4 wherein said operating member controls said locking mechanism to restrict length variation when aligned in said walking cycle rear position and to permit length variation when aligned in said walking cycle front position.

* * * * *